United States Patent [19]

Böhm

[11] 4,130,396
[45] Dec. 19, 1978

[54] METHOD FOR THE QUANTITATIVE ANALYSIS OF Al-C- AND Al-H- BONDS IN HYDROCARBONS

[75] Inventor: Ludwig Böhm, Mainz, Fed. Rep. of Germany

[73] Assignee: Hoechst Aktiengesellschaft, Frankfurt am Main, Fed. Rep. of Germany

[21] Appl. No.: 800,911

[22] Filed: May 26, 1977

[30] Foreign Application Priority Data

May 29, 1976 [DE] Fed. Rep. of Germany ....... 2624204

[51] Int. Cl.$^2$ ..................... G01N 21/06; G01N 31/16
[52] U.S. Cl. ............................... 23/230 M; 23/230 R
[58] Field of Search ......................... 23/230 R, 230 M

[56] References Cited

PUBLICATIONS

D. E. Jordan, Anal. Chem. 40(14), 2150–2153 (1968).
Chemical Abstracts, 70:43932t (1969).

Primary Examiner—Sidney Marantz
Attorney, Agent, or Firm—Curtis, Morris & Safford

[57] ABSTRACT

For quantitative analysis of aluminum compounds containing Al—C— and Al—H— bonds in hydrocarbons the organo-aluminum compounds are decomposed with a lower alcohol and the excess alcohol is subjected to back titration with the solution of a colored compound of an alkali metal with a polynuclear aromatic hydrocarbon.

1 Claim, 1 Drawing Figure

U.S. Patent    Dec. 19, 1978    4,130,396
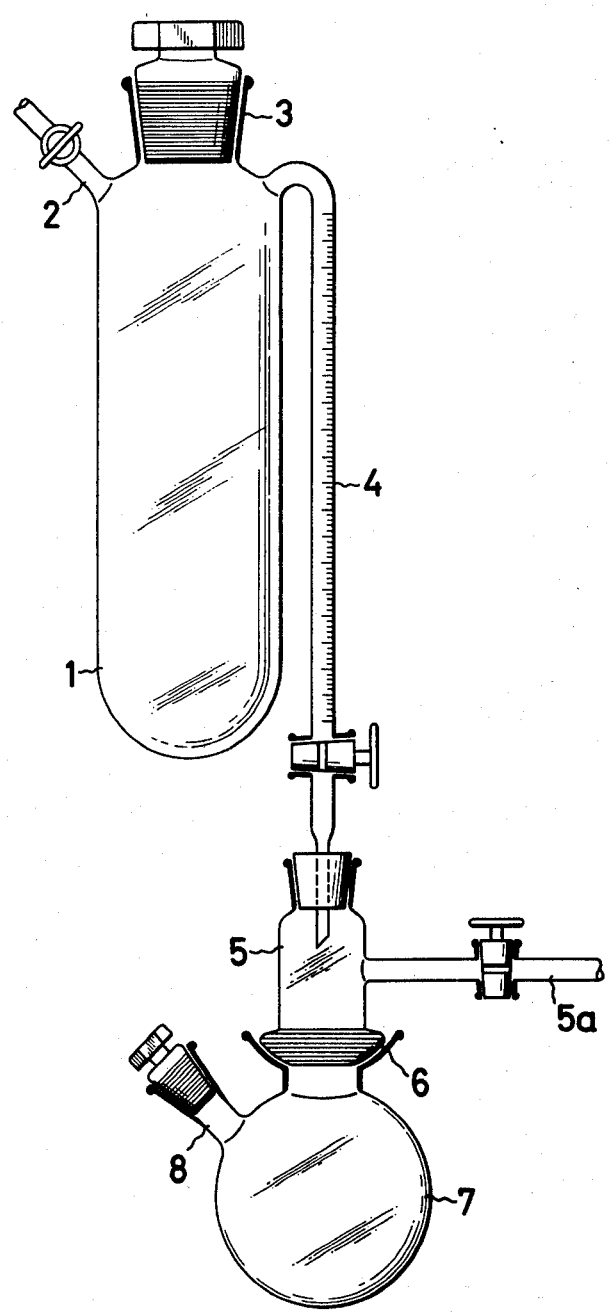

METHOD FOR THE QUANTITATIVE ANALYSIS OF AL-C- AND AL-H- BONDS IN HYDROCARBONS

There is a series of industrially interesting processes, in which organoaluminum compounds are used as catalysts or as co-catalysts, for example, in the low pressure polymerization of α-olefins according to the methods of Ziegler and Natta. In this case the organoaluminum compounds are present predominantly in relatively low concentrations ($<10$ mmoles/dm$^3$). It is of considerable interest to quantitatively analyze the concentration of the organoaluminum compounds in this concentration range.

A series of analyzing methods for the quantitative analysis of organoaluminum compounds is described in the literature (see T. R. Compton, Analysis of Organoaluminium and Organozinc compounds, Pergamon Press 1968, and H. Lehmkul, K. Ziegler in Houben-Weyl, Methoden der Organischen Chemie 13/4, 291, (1970)). All the methods described can only be applied at relatively high concentrations. None of the methods can be used in the concentration range of $<10$ mmoles/dm$^3$. However, this is the concentration range present, for example in the low pressure polymerization of α-olefins.

It has now been discovered that "active" aluminum can be analyzed quantitatively even in the concentration range of $<10$ mmoles/dm$^3$, if the aluminum compound is decomposed with an alcohol and the unreacted alcohol is subjected to back titration with a colored organometallic compound.

The subject matter of the invention is thus a process for the quantitative determination of the content of Al—C— and Al—H— bonds in hydrocarbons, which comprises decomposing the organoaluminum compounds with a lower alcohol and subjecting the excess alcohol to back titration with the solution of a colored organometallic compound of an alkali metal with a polynuclear aromatic hydrocarbon.

According to the process of the invention, the organoaluminum compound is quantitatively decomposed with an excess of a lower alcohol for example methanol, ethanol, isopropanol, n-propanol, and butanols, preferably methanol, at room temperature, or, if necessary, even at a higher temperature. The temperature for the decomposition is from 10° to 100° C., preferably from 20° to 70° C. The Al—C— and Al—H— bonds are split off as hydrocarbons or as H$_2$ and replaced by the alkoxy group. It is irrelevant whether other groups as well (for example higher alcohols or halogen) are split off from the Al with the alcohol, because these groups again have an acid H-atom like the alcohol which, during the back-titration with an organometallic compound, is likewise detected in addition to the alcohol still present.

The excess alcohol or the acid H-atoms are subjected to back titration after the decomposition. The alkali metal compounds of polynuclear aromatic substances, such as naphthalene or anthracene for example, have proved to be suitable reagents.

They may be prepared by direct reaction of the alkali metals with the aromatic substances in a polar organic solvent, preferably ethers, (for example, tetrahydrofuran, dioxan, dimethoxyethane) at room temperature, (compare H. F. Ebel, A. Lüttringhaus in Houben-Weyl, Methoden der Organischen Chemie 13/1 254 (1970)). The compounds resulting thereby are deep blue or green and lose their color in the reaction with H-acid compounds such as methanol. In the titration, the end product can therefore easily be recognized, and an indicator does not have to be added. The concentration of the organometallic compound should be from 0.05 to 0.5, preferably from 0.1 to 0.2 molar.

As these compounds are sensitive to O$_2$ and H$_2$O, they have to be handled under a protective gas (Ar, N$_2$).

DESCRIPTION OF THE DRAWING

The FIGURE generally depicts an arrangement of apparatus suitable for carrying out the inventive process. An anthracenyl-sodium solution is prepared and stored in the apparatus shown in the FIGURE and the titration also is carried out in it.

The various components of the apparatus will be described below. For the titration, the burette is filled by tipping the Schlenk tube. The burette is then placed on the flask. This apparatus corresponds to a large extent to an apparatus specified in the literature (compare H. Metzger, E. Müller, in Houben-Weyl, Methoden der Organischen Chemie, I/2, 321, (1959), Diagram 72, page 373).

This apparatus consists of a Schlenk tube 1, having a connecting tube 2 and a filling opening 3. The Schlenk tube has a capacity of preferably 1 liter, the inlet opening 3 is provided with an NS 29. A burette 4 is fused onto the Schlenk tube at the top and holds preferably 10 ml. The outlet of the burette is placed in a spacer piece 5 which permits the introduction of a protective gas through the tube 5a, and is joined to the titration flask 7 by means of a ground ball-and-socket joint 6. The titration flask has a connecting tube 8 through which the protective gas can flow of the solution to be titrated can be introduced. It holds preferably 250 ml. The contents of the Schlenk tube and the titration flask can be stirred by a magnetic stirrer.

EXAMPLE

1. Purification of tetrahydrofuran (THF)

Apparatus: Distilling apparatus with overlying protective gas; 4 liter capacity round-bottomed flask; silver jacket column (80 cm) filled with Raschig rings; top of column for adjusting the reflux ratio.

2.5 liters of THF are boiled for about 4 hours over sodium-potassium alloy under the reflux, than the THF is distilled under protective gas at a reflux ratio of 1:1. After the first runnings have been removed, the condenser is replaced by the tube indicated in the enclosure. About 1 liter of THF is then distilled.

2. Purification of anthracene 300 g of toluene and 39 g of anthracene are placed in a 500 ml Erlenmeyer flask equipped with a magnet stirrer and are heated to 100° C. while stirring. The anthracene thereby dissolves. After the addition of two spatula tips of active charcoal and repeated thorough mixing, filtration is carried out hot over a folded filter. After cooling to room temperature, the crystals precipitated are suctioned off on a suction filter and washed with cold toluene. The anthracene thus purified is dried under a vacuum in the dessicator and preserved over blue gel.

3. Preparation of anthracenyl-sodium

In the apparatus shown in FIG. 1, 200 mmole (= 4.6 g) of finely chopped sodium are added to the THF. 100 mmoles (= 17.8 g) of anthracene are then added. The additions are always made under a flow of protective gas. The deep blue color of the anthracenyl-sodium occurs immediately. The formation of the anthracenyl-sodium is effected while stirring at room temperature and is complete after a few hours (for example, overnight).

4. Analysis of titer

To analyze the titer, 50 ml of a hydrocarbon (for example n-hexane) is introduced as solvent into the apparatus described and is titrated with the anthracenyl-sodium solution to decomposition in order to destroy the impurities still present. The titration is effected under protective gas. 50 µl of methanol are then injected under a protective gas and the titration is carried out, while stirring, until a sudden change in color. The titer x is calculated according to the following equation:

$$x = 1.235/V_1$$

x = titer in mmoles/ml
$V_1$ = volume of the anthracenyl-sodium solution which was required to react with 50 µl of methanol.

The value of 1.235 indicates the number of millimoles which correspond to 50 µl of methanol.

5. Analysis of the concentration of the "active" aluminum in hydrocarbons

The sample to be analyzed is in a 1 liter tiltable tube. Under a protective gas, 50 µl of methanol are added per 100 ml of sample. Methanol must always be present in excess. The sample is shaken then and is then left to stand for 1 hour at room temperature (for example, with Al(C$_2$H$_5$)$_3$), or at 60° C. (for example, with Al-isoprenyl). The decomposition is then complete. After the decomposition, the volume of the solution is determined (at room temperature or at 60° C.).

For the back titration of the methanol still present, 100 ml of the solution is taken away, again under protective gas, this sample is introduced into the heated titration flask, cooled under protective gas, and the unconsumed methanol is subjected to back titration with anthracenyl-sodium. The end product of the titration is distinguished by the sudden change from colorless or weakly yellow to deep blue.

To calculate the concentration of the "active" aluminum the following variables must be know:

V = volume of the sample at room temperature or at 60° C. in ml. v = volume of the methanol added in µl. $V_2$ = anthracenyl-sodium solution consumed in the back titration for 100 ml of the sample, with the titer x in ml.

The concentration of the active aluminum at room temperature (25° C.) is calculated according to the following equation:

$$[AlR_3] = 10/3 \cdot (2.47 \cdot v/V \cdot f - x \cdot V_2).$$

The factor f gives the ratio of the densities of the solvent used at 25° C. and at 60° C. When the decomposition at 25° C. was carried out, the factor is 1.

The concentration [AlR$_3$] ("active" aluminum) is given in mmoles/dm$^3$.

This method enables the Al—C— and Al—H— bonds to be anayized in the concentration range of <10 mmoles/dm$^3$ within a limit of error of at most 10% with a statistical reliability of 95%. This result was obtained for Al(C$_2$H$_5$)$_3$ and for aluminum sesquichloride, as the following values show:

Analysis of the Al—C—bonds in Esso-Varsol. All values are calculated on AlR$_3$ or Al$_2$R$_3$Cl$_3$.

| Sample | Al-C/mmole | AlEt$_3$/mmole Al$_2$Et$_3$Cl$_3$/mmole |
|---|---|---|
| 0.515 mmoles of AlEt$_3$ in | 1.68 | 0.56 |
| 100 ml of Esso-Varsol | 1.45 | 0.48 |
|  | 1.30 | 0.43 |
|  | 1.34 | 0.45 |
|  | 1.58 | 0.53 |
|  | 1.74 | 0.58 |
|  | 1.44 | 0.48 |
|  | 1.44 | 0.48 |
|  | 1.47 | 0.49 |
|  | 1.69 | 0.56 |
|  | 1.60 | 0.53 |
|  | 1.77 | 0.59 |
|  | 1.64 | 0.55 |
|  | 1.59 | 0.53 |
|  | 1.68 | 0.56 |
|  | 1.71 | 0.57 |
| 0.493 mmoles of Al$_2$Et$_3$Cl$_3$ | 0.66 | 0.44 |
| in 100 mol of Esso-Varsol | 0.78 | 0.52 |
|  | 0.77 | 0.52 |
|  | 0.68 | 0.45 |

Each sample was decomposed for 60 minutes with 100 µl of CH$_3$OH ≙ 2.47 mmoles; the excess alcohol was subjected to back titration with Na-anthracenyl; Et = —C$_2$H$_5$.

What is claimed is:
1. A process for the quantitative analysis for the content of organoaluminum compounds containing Al—C— and Al—H— bonds in hydrocarbons, which comprises decomposing said organoaluminum compounds with a lower alcohol and subjecting an excess of said alcohol to back titration with a solution of a colored organometallic compound of an alkali metal and a polynuclear aromatic hydrocarbon.

* * * * *